United States Patent [19]

Ness

[11] Patent Number: 4,549,051

[45] Date of Patent: Oct. 22, 1985

[54] INDUCTION HEATING DEVICE FOR NOZZLES OF CONTAINERS

[76] Inventor: Richard A. Ness, Rte. 2, Box 280, Battle Lake, Minn. 56515

[21] Appl. No.: 580,343

[22] Filed: Feb. 15, 1984

[51] Int. Cl.[4] ............................................... H05B 6/00
[52] U.S. Cl. .......................... 219/10.49 R; 219/10.43; 219/10.57; 604/291
[58] Field of Search ............... 219/10.71, 10.73, 10.77, 219/10.43, 10.69, 10.57, 10.49 R, 214, 10.41; 604/291; 363/15, 109

[56] References Cited

U.S. PATENT DOCUMENTS

| | | | |
|---|---|---|---|
| 1,381,500 | 6/1921 | Reader | 219/ |
| 1,862,120 | 6/1932 | Northrup | 219/10.57 |
| 2,809,264 | 10/1957 | Van Iperen | 219/10.79 |
| 2,875,311 | 2/1959 | Harkenrider | 219/10.49 R |
| 3,342,970 | 9/1967 | Emeis | 219/10.79 |
| 3,485,244 | 12/1969 | Rosen | 128/254 |
| 3,518,393 | 6/1970 | Besseling et al. | 219/10.41 |
| 3,535,481 | 10/1970 | Korb | 219/10.41 |
| 3,578,945 | 5/1971 | Ayres | 219/214 |
| 3,816,687 | 6/1974 | Heitner | 219/10.49 R |
| 3,931,564 | 1/1976 | Mims | 363/15 X |
| 3,934,585 | 1/1976 | Maurice | 128/225 |
| 4,265,922 | 5/1981 | Tsuchiya et al. | 219/10.69 X |

*Primary Examiner*—Roy N. Envall, Jr.
*Assistant Examiner*—M. M. Lateef
*Attorney, Agent, or Firm*—Merchant, Gould, Smith, Edell, Welter & Schmidt

[57] ABSTRACT

The present device includes a primary coil wound on a spool having an opening at one end for receiving the nozzle of a container. The coil is connected to an alternating current source. The nozzle of the container has a conductive portion which functions as a secondary inductor having internal resistance. Current is induced and dissipated in the conductive portion thereby heating the portion and the substance contained therein.

17 Claims, 8 Drawing Figures

U.S. Patent Oct. 22, 1985 Sheet 1 of 2 4,549,051
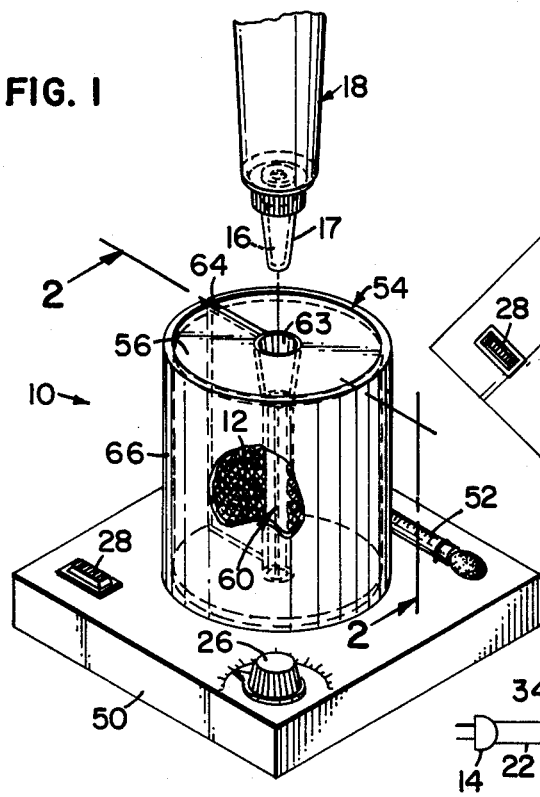
FIG. 1
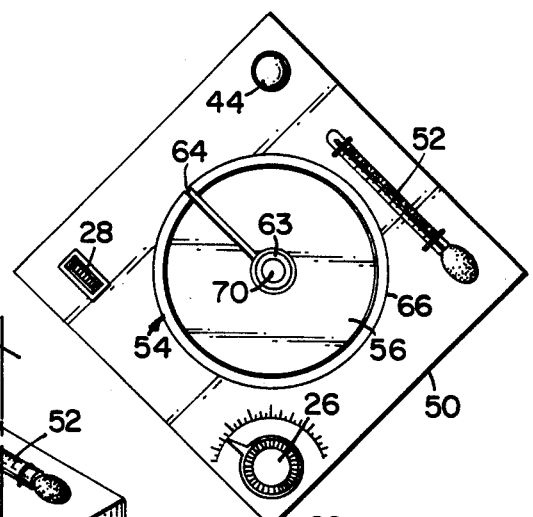
FIG. 4
FIG. 5
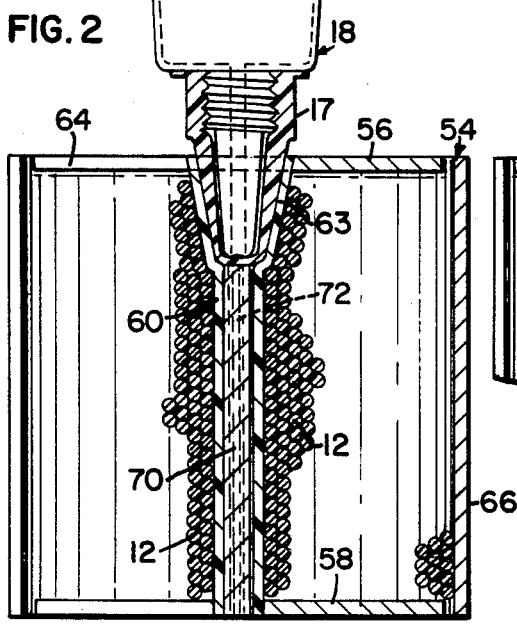
FIG. 2
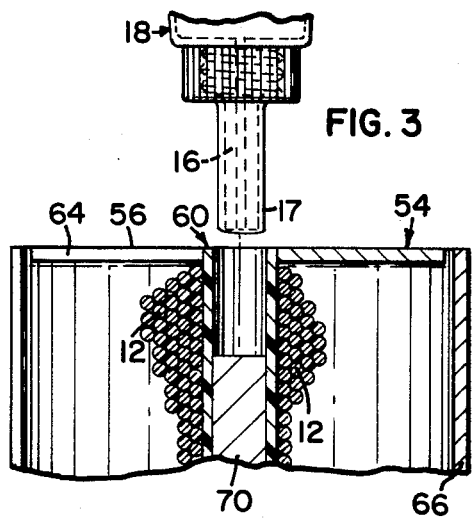
FIG. 3

INDUCTION HEATING DEVICE FOR NOZZLES OF CONTAINERS

FIELD OF THE INVENTION

The present invention is directed to a device for heating nozzles of containers carrying various gel or liquid substances. The substances are commonly medications and the intent is to warm a small amount of the substance contained in the nozzle of the container, without affecting the larger amount contained in the container, to overcome body shock when the otherwise cold substance is applied to a human or animal subject.

BACKGROUND OF THE INVENTION

The thermal shock of receiving a cold substance on the body is a well known experience to everyone. Various home methods have been devised to warm bottles and containers before application of substances therein to humans or animals. In many cases, it is acceptable to warm the entire container each time an application is made if the substances therein are heat stable. In some cases, however, such repetitive warming can lead to degradation of the substance. For example, eye ointments are frequently comprised of a solidified mineral oil including petroleum and mineral oils along with chlorbutinol or paraben as a bacterial static agent in such combination that the ointment is a gel at ambient room temperature (e.g. 70° F.) and a liquid at body temperature (98.6° F.). Such ointments are advantageous in that almost any medication can be incorporated therein. In particular, medications may be ground into a fine almost colloidal size particle for suspension throughout the ointment, or aqueous solutions may be mixed with the ointment to form an emulsified water and oil suspension. In any case, repeated heating of either mixture would undoubtedly cause the colloidal particles or emulsified suspensions to separate from or congregate within the dependent portion of the mixture. Application of such mixture could then become unhelpful or dangerous because of uneven concentrations.

Continuing with the example of the gel-type eye ointment, such ointment is advantageous since the specific heat of the ointment does not cause abrupt thermal discomfort when the ointment is applied to an aye. The problem, however, is that a ribbon of the ointment must be squeezed from a tube and it is next to impossible to squeeze one drop or any other measured quantity. Frequently, an excessive amount is applied resulting in blurred vision because of the excess or resulting in some excess being squeezed out between the lids of the eye onto the surrounding skin and causing messy cosmetic problems, etc.

There have been attempts to design apparatus to preheat unit dose medications before application. For example U.S. Pat. No. 3,934,585 shows in FIG. 10 heating coils for both the dispensing tube itself and the end of the dispensing tube. The coils are resistive and become hot so that heat is transferred by conduction through the dispensing tube to the substance therein. The apparatus is obviously limited in its usefulness for reasons as discussed above as well as the necessity to shield surrounding objects from the heated coils and the necessity to make good thermal contact between the heated coil and the end of the dispensing tube.

SUMMARY OF THE INVENTION

The present invention is directed to an induction heating device. For the present device, at least a portion of the nozzle of the container is electrically conductive. The device includes an electrical circuit having a primary inductor and a source of alternating or radio frequency current. The device further includes mechanism for receiving the nozzle of the container in an end of the primary inductor. The electrically conductive portion of the nozzle forms a secondary inductor in which the magnetic field from the primary inductor creates an induced current. The current is dissipated by the internal resistance of the conductive portion thereby heating the portion and, consequently, the substance within the nozzle while the nozzle is within its sterile protective cap.

In one embodiment of the heating device, mechanism for concentrating the magnetic field is used and includes a core of ferromagnetic material within at least a portion of the primary inductor as well as end plates at opposite ends of the primary inductor and a cover for surrounding the walls between the ends. Slots are formed between center openings and outside edges of the end plates and between opposite ends of the cover to prevent the induction of eddy currents in the concentrating elements. Also, separation of the end plates, the cover and the core from one another further prevent unwanted induced currents.

In another embodiment of the device, the nozzle of the container is non-conductive. Rather, a metallic conductive insert is inserted into the nozzle. The insert preferably includes a flange substantially perpendicular to the axis of the nozzle. An eddy current is induced and dissipated in the insert thereby heating the insert and immediate surrounding material. That is, since many containers are made from a plastic or similar material, they are relatively good thermal insulators. The metal insert is a good heat conductor. Therefore, when the induced current dissipates to warm the insert, the insert warms only material in its immediate vicinity. This embodiment is particularly advantageous since it may be used with containers holding aqueous solutions.

For many substances, a warming time may be determined. Usually, the warming time is a direct function of the difference in temperature between ambient temperature and some known temperature, such as body temperature. Consequently, yet another embodiment of the warming device includes a thermometer and a variable timing switch for controlling the on-time of the primary inductor circuit. Thus, a simple calculation of the temperature difference implies a heating time which can be set as appropriate with the timer.

The present heating device is particularly advantageous since the electrically conductive nozzle or metallic flanged insert and the receiving mechanism in the primary inductor, along with the magnetic field concentrating elements combine to provide a heating region for a single drop or dose of a liquid or a gel substance. Furthermore, the nozzle and substance therein heats while the nozzle is covered by an electrically non-conductive and thermally heat insulating cap so that the nozzle and substance therein remain sterile.

The device may be used for office or home use wherever standard 60 cps alternating current is available, or it may be designed for use as a portable unit with DC-AC alternator or inverter. The more stationary type units would be particularly beneficial for physicians and others who have a continual need for warming the nozzle of a container, while the portable units would be more applicable for persons needing to warm an appropriately contained substance at regular intervals regardless of where they are. For example, glaucoma patients must apply medication to their eyes at very regular intervals. A portable unit would be particularly advantageous for an active, mobile, glaucoma-afflicted person.

The present heating device is directed to and does solve the thermal shock problem for application of a drop or two or single dose of medication or other substance. Furthermore, the device is uncomplicated and safe. As indicated, the device may be made for stationary use or in a portable fashion having a battery and DC-AC alternator or inverter.

These advantages and other objects obtained with this invention are further explained and, consequently, may be better understood by reference to the drawings and descriptive matter which follows hereinafter. A preferred embodiment of the invention and other embodiments are illustrated and described in detail.

BRIEF DESCRIPTION OF THE DRAWINGS

FIG. 1 is a perspective view of a heating device in accordance with the present invention;

FIG. 2 is a cross-sectional view of the device of FIG. 1;

FIG. 3 is a cross-sectional view similar to FIG. 2 but showing an alternate embodiment;

FIG. 4 is a top plan view of the device of FIG. 1;

FIG. 5 is an electrical schematic applicable for the embodiments of FIGS. 1-4;

BRIEF DESCRIPTION OF THE PREFERRED AND OTHER EMBODIMENTS

Figure 6:
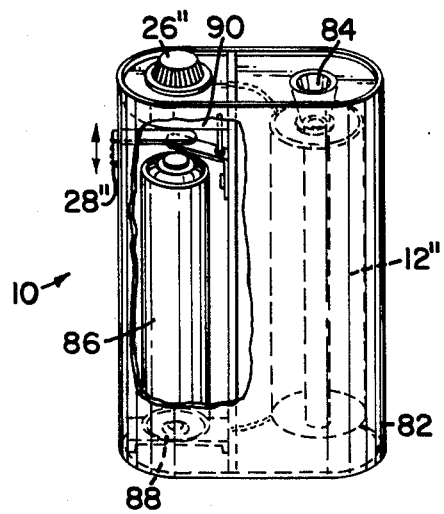
FIG. 6 is a perspective view of a portable embodiment of the device.

Referring now to the drawings wherein like reference numerals designate identical or corresponding parts throughout the several views, and more particularly to FIG. 1, a preferred heating device in accordance with the present invention is designated generally by numeral 10. Device 10 includes a primary inductor 12 connected to a source of alternating current. Inductor 12 is formed as a coil such that a nozzle 16 and a cap 17 of a substance containing container 18 may be inserted in one end of the coil 12. Nozzle 16 is made of a conductive material such that the variable magnetic field associated with the alternating current in the primary inductor induces an eddy a current in nozzle 16 according to Faraday's law of electromagnetic induction. Essentially, the nozzle 16 functions as a one turn secondary coil having internal resistance. Current is induced and dissipated, therefore, in the conductive nozzle 16. The dissipated current heats the nozzle 16 thereby heating substance within the nozzle 16 and cap 17.

As schematically illustrated in FIG. 5, the plug 14 for connection to an alternating current source (not shown) is preferably connected through a fuse 20 via lines 22 and 24 to inductor 12. The other side of inductor 12 is connected through a variable timer 26 and a switch 28 via lines 30, 32, 34 to plug 14. Nozzle 16 is schematically represented in FIG. 5 by an equivalent circuit including a secondary inductor 36 and a resistor 38. If desired, indicator bulb 44 may be connected in parallel with primary inductor 12, for example, with lines 46, 48.

As shown in FIGS. 1-3, primary inductor or coil 12 is mounted on a base 50. Base 50 houses switch 28, timer 26, light 44, fuse 20 and all the necessary wiring. Switch 28, timer 26, and bulb 44 are shown as being operable and visible in and from the top of base 50. It is understood that other arrangements may be equally functional. Switch 28 is shown as a push button type switch. Other switch configurations, such as toggle switches, are equally applicable. Similarly, the light could be any type of indicator, for example, a buzzer. It is preferable that timer 26 be adjustable. In any case, switch 28, timer 26, bulb 44 and fuse 20 are commercially available in a variety of configurations. A thermometer 52 or other type of ambient temperature indicator is also preferably attached to base 50 for a purpose indicated hereinafter.

Coil 12 is constructed on a spool 54 such that magnetic concentrating elements are provided for a substantial portion of the magnetic circuit for the field of the primary inductor. Spool 54 includes upper end plate 56 and lower end plate 58 held spaced apart by a hollow form 60. End plates 56, 58 are preferably ferromagnetic so as to have a high magnetic permeability, while form 60 is nonmagnetic. End plates 56, 58 each have a slot 64 extending from form 60 to the outer edge of the particular plate. Slots 64 minimize the formation of eddy currents in the plates. The upper end of form 60 is shaped to receive nozzle 16 and cap 17. Preferably, nozzle 16 extends into coil 12 so that it passes through at least one and preferably several more planes of individual windings of coil 12. The most usual shape for a nozzle 16 is frusto-conical. So that nozzle 16 is not contaminated by contacting form 60, it is usually preferable to keep a cap 17 on nozzle 16 when it is inserted into the receiving portion 63 of form 60. As shown in FIG. 5, however, a nozzle may assume other shapes including a perfectly cylindrical shape, and it may be used with device 10 without having a cap 17.

Surrounding coil 12 is a cover 66. Cover 66 is also a magnetic concentrating element and, consequently, preferably ferromagnetic. In addition, cover 66 has a slot 68 (see FIG. 4) which, like slots 64, minimizes the formation of eddy currents in cover 66. It is noted that end plates 56, 58 are spaced from cover 66 for the further purpose of minimizing the formation of eddy currents.

A further magnetic concentrating element is preferably included in the form of a rod or rods 70 which fits within form 60. Rod 70 is ferromagnetic and preferably has a plurality of longitudinal slots 72, or may be comprised of a plurality of separate, smaller rods. The nonmagnetic material of form 60 spaces rod 70 from end plate 58 and, again, minimizes any unwanted eddy currents. Similarly, the longitudinal slots 72 minimize any current flow in rod 70. The minimization or possibly elimination of eddy currents maximizes the magnetic field of coil 12 thereby maximizing the induced current created in nozzle 16.

Figure 8:
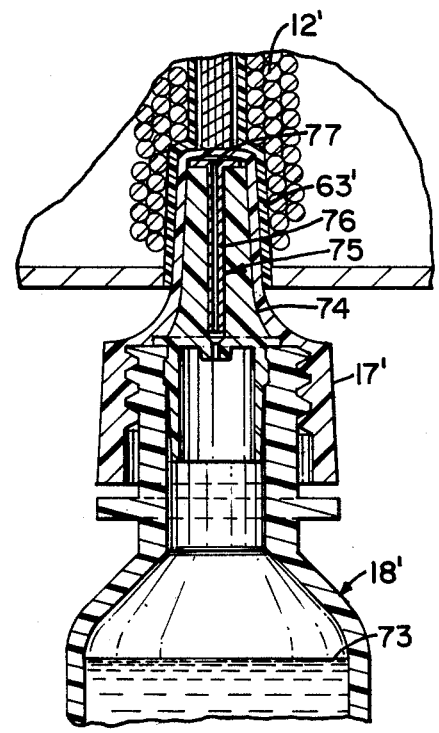
FIG. 8 is a cross-sectional view of yet another embodiment.

In FIG. 8, an alternate embodiment of the present invention is shown. Container 18' is shown in the form of a bottle containing an aqueous solution 73. A plug 74 fits into the upper opening of bottle 18' and is shaped in the form of a nozzle. Cap 17' fits over the nozzle shape of plug 74 to screw onto the threaded neck of bottle 18'. In this fashion, cap 17' keeps nozzle 74 and the solution 73 sterile until application. Such bottles 18' with plugs 74 and caps 17' are conventional. The plug 74 is commonly electrically non-conductive. Thus, to provide for the induced current and resultant heating of the present invention, a conductive insert 75 is inserted into the axial passage of plug 74. Insert 75 has a tubular portion 76 and a flange portion 77. The tubular portion 76 fits within the axial passage of plug 74 until flange 77 contacts the tip of the nozzle shape of plug 74. Cap 17' is insertable in a receiving portion 63' of a coil 12' as described hereinbefore. In this way, the magnetic field of coil 12' cuts through insert 75, and primarily flange 77, to induce a current therein. The heat caused by dissipation of the induced current is conducted throughout insert 75. On removal of bottle 18' and cap 17' from coil 12', bottle 18' is inverted so that a drop or so of solution 73 may enter the axial passage of insert 75 to be warmed thereby. On slightly squeezing bottle 18', the warmed drop falls out for application as desired.

Figure 7:
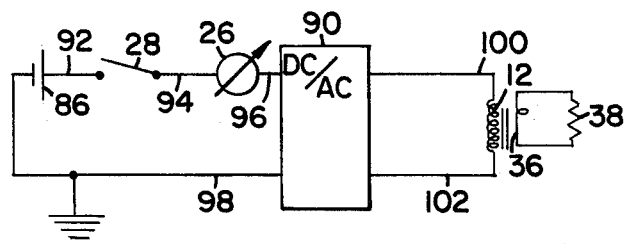
FIG. 7 is an electrical schematic applicable for the device of FIG. 6.

A portable embodiment of the present invention is shown in FIGS. 6–7 and designated 10". Device 10" includes a housing 82 containing a coil 12". Coil 12" may be constructed on a spool with magnetic concentrating elements in a fashion described hereinbefore. In any case, one end of coil 12" cooperates with an opening 84 in housing 82 to receive a nozzle and cap of a container in the fashion described hereinbefore. Another portion of housing 82 contains a battery or cell 86. One end of cell 86 is grounded as at 88 while the other end is connectable to switch 28". A direct conventional current to alternating current integral circuit (IC) chip 90 is located within housing 82 and connected with coil 12". A variable timer 26" is also shown at one end of housing 82. As with the earlier embodiments, an ambient temperature indicating device and a light for indicating when the circuit is closed could also be features of a portable device 10".

An exemplary electrical circuit is schematically shown in FIG. 7 for device 10". Cell 86 is connected through switch 28" and timer 26" to DC/AC converter 90 via lines 92, 94 and 96. The other side of cell 86 is grounded and connected via line 98 to a second terminal of converter 90. A third terminal of converter 90 is connected through timer 26" to one end of coil 12" via lines 100, while a fourth terminal of converter 90 is connected via line 102 to the other end of coil 12". As in FIG. 5, the equivalent circuit of a nozzle or an insert, like 74, is represented by secondary inducator 36" and resistor 38".

In operation, a chart relating time of operation to the temperature difference between ambient temperature and body temperature could be prepared for various medicines and substances which would be heated with device 10. A reading of thermometer 52 could be used in conjunction with the chart to determine a setting for timer 26. The nozzle and cap 17 of 16 of container 18 holding the appropriate substance is then inserted into the appropriate receiving end of spool 54. Switch 28 is turned on. Bulb 44 lights up to show that the circuit has been completed. When bulb 44 goes out, switch 28 is turned off and container 18 removed from device 10. A drop or two of the liquified substance within container 18 may then be dropped from nozzle 16 for appropriate application by light pressure on container 18.

It is understood that timer 26 and thermometer 52 could be a single device and could, in fact, be self regulating so as to operate automatically when switch 28 is switched on.

As the alternating current in inductor 12 rises and falls, the associated magnetic field similarly builds and collapses. The field is concentrated fairly well by end plates 56, 58, cover 66 and rod 70. More particularly, a highly concentrated portion of the varying magnetic field extends vectorially between end plate 56 and rod 70. That is, much of the field cuts through the conductive portion of nozzle 16. In this way, nozzle 16 functions as a one turn inductor such that the rising or collapsing field induces a current having its own associated field which rises to oppose the inducing field. The induced current is rapidly dissipated within the internal resistance of the nozzle. In that way, however, the nozzle heats. The heated nozzle, of course, transfers the heat to the substance, likely a gel or aqueous solution, contained therein thereby warming it. The timer allows this process to continue until the timer has run out which from previous experience indicates that the substance has reached approximately the desired temperature.

As indicated hereinbefore, the present invention is particularly advantageous for eliminating the "thermal shock" which occurs when a cold substance is applied to a human or animal body, expecially in the case of eye drops to eyes. In addition, the present invention is advantageous in that only the portion of the substance which will be used is heated so that the remainder of the substance is not subjected to unnecessary heating which may cause degradation of the substance. Furthermore, in the case of a gel only the small amount of substance that is heated is expelled from the nozzle thereby representing an economy and conservation of the substance oftentimes an expensive medication. The possibility of over-dosage is vastly reduced also.

As shown by the various embodiments, the present invention may be practiced with a portable unit or a desk top unit. A storage battery source of energy or the usual 110 AC commercial source may be used. A variety of nozzle and cap shapes and mating receivers are applicable. In addition, an embodiment is shown wherein a conductive insert is usable in conjunction with a non-conductive nozzle, as in a dropper squeeze bottle.

Even though these advantages and alternatives of the invention, as well as details of structure and function have been set forth, it is understood that the disclosure is illustrative only. Consequently, changes made, especially in matters of shape, size, arrangement, and thermal regulatory/timing circuits, to the full extent extended by the general meaning of the terms in which the appended claims are expressed, are within the principle of the invention.

What is claimed is:

1. An induction heating device for an electrically conductive portion of a nozzle of a container separate from said device, said container containing a substance for ejection from said nozzle, said device comprising:

an electrical circuit including a primary inductor and a source of alternating current, said alternating current through said primary inductor creating a magnetic field; and means for receiving said nozzle by insertion of said nozzle in an end of said primary inductor, said conductive portion of said nozzle forming a secondary inductor in which the magnetic field from said primary inductor creates an induced current in said conductive portion for dissipation therein thereby heating said conductive portion and said substance within said conductive portion of said nozzle.

2. The device in accordance with claim 1 including means for concentrating the magnetic field said concentrating means including a core of ferromagnetic material within a portion of said primary inductor, first and second plates at the ends of said primary inductor and a cover about said primary inductor between said plates, said plates and said cover being ferromagnetic.

3. The device in accordance with claim 2 including means for minimizing eddy currents in said concentrating means.

4. The device in accordance with claim 3 wherein said minimizing means includes a slot in each of said first and second plates.

5. The device in accordance with claim 3 wherein said minimizing means in said cover includes a slot between opposite open ends of said cover.

6. The device in accordance with claim 3 wherein said core is comprised of a plurality of rods.

7. The device in accordance with claim 3 wherein said core, said cover and said plates are spaced apart from one another.

8. The device in accordance with claim 1 including means for controlling said electrical circuit relative to heat needed to warm said substance within said conductive portion to a desired temperature.

9. The device in accordance with claim 8 wherein said controlling means includes means for sensing ambient temperature operably connected to means for switching said circuit off.

10. The device in accordance with claim 1 including an insert for said nozzle, said insert forming the conductive portion of said nozzle, said insert including a tubular portion and a flange, said tubular portion fitting within said nozzle so that said nozzle contacts said flange.

11. In apparatus for warming a small quantity of substance in a container, the combination comprising:
    an electrically-conductive nozzle for said container;
    an electrical circuit including a primary inductor and means for electrically energizing said primary inductor with an alternating current, the alternating current through said primary inductor creating a magnetic field, said primary inductor being comprised of a coil with a plurality of wire windings; and
    means for receiving by insertion of said nozzle in an end of said coil, said receiving means being formed to allow said nozzle to extend through at least one of said windings, said nozzle forming a secondary inductor in which the magnetic field from said primary inductor creates an induced current in said nozzle for dissipation within said nozzle thereby heating said nozzle and said substance within said nozzle;
    whereby on removal of said nozzle from said receiving means, the warmed substance in said nozzle may be dispensed.

12. The combination in accordance with claim 11 including a protective cap for said nozzle, said protective cap being electrically an insulator, said receiving means being shaped to snugly receive said protective cap.

13. The combination in accordance with claim 11 wherein said receiving means in a cylindrical cavity at the end of said coil.

14. The combination in accordance with claim 11 wherein said energizing means includes a direct current producing cell and means for converting the direct current to alternating current.

15. An induction heating apparatus for a portion of a container of substance, said container having a nozzle, said apparatus comprising the combination of:
    an electrically conductive insert for said nozzle, said insert having a first portion for fitting within said nozzle for contact with substance therein, said nozzle having a centerline, said insert further having a second portion substantially perpendicular to the centerline of said nozzle;
    an electrical circuit including a primary inductor and means for electrically energizing said primary inductor with an alternating current, the alternating current through said primary inductor creating a magnetic field, said primary inductor being comprised of a coil with a plurality of wire windings; and
    means for receiving said nozzle in an end of said coil, said receiving means being formed to allow said nozzle to extend through said windings so that said insert extends through at least one of said windings, said insert forming a secondary inductor in which the magnetic field from said primary inductor creates an induced current in said insert for dissipation within said insert thereby heating said insert and said substance in contact with said insert.

16. A method for heating a small quantity of substance within a container, said container having a nozzle for ejecting the substance, said nozzle having a conductive portion, said method comprising the steps of:
    inserting said nozzle in one end of a primary inductor;
    energizing an electrical circuit, said circuit including an alternating current source and said primary inductor, the conductive portion of said nozzle functioning as a one turn secondary inductor whereby current is induced and dissipated in said conductive portion to heat said nozzle and substance contained therein;
    removing said nozzle from the end of said coil; and
    ejecting the warm substance within said conductive portion toward an appropriate receiver.

17. The method of claim 16 including the steps of turning on the electrical circuit for a predetermined time, said nozzle remaining in the end of said coil for the predetermined time.

* * * * *

UNITED STATES PATENT AND TRADEMARK OFFICE
CERTIFICATE OF CORRECTION

PATENT NO. : 4,549,051
DATED      : October 22, 1985
INVENTOR(S) : Richard A. Ness It is certified that error appears in the above-identified patent and that said Letters Patent is hereby corrected as shown below:

Column 1, line 48, delete "aye" and insert therefor --eye--.
Column 3, line 55, delete "a".
Column 5, line 48, delete "inducator" and insert --inductor--.

Signed and Sealed this

Twenty-first Day of January 1986

[SEAL]

Attest:

DONALD J. QUIGG

Attesting Officer

Commissioner of Patents and Trademarks